United States Patent
Hemp et al.

(10) Patent No.: US 7,072,775 B2
(45) Date of Patent: Jul. 4, 2006

(54) VISCOSITY-CORRECTED FLOWMETER

(75) Inventors: John Hemp, Bedford (GB); Hoi Cheong Yeung, Bedford (GB)

(73) Assignee: Invensys Systems, Inc., Foxboro, MA (US)

(*) Notice: Subject to any disclaimer, the term of this patent is extended or adjusted under 35 U.S.C. 154(b) by 0 days.

(21) Appl. No.: 10/873,651

(22) Filed: Jun. 23, 2004

(65) Prior Publication Data

US 2005/0022611 A1 Feb. 3, 2005

Related U.S. Application Data

(60) Provisional application No. 60/482,537, filed on Jun. 26, 2003.

(51) Int. Cl.
*G06F 19/00* (2006.01)

(52) U.S. Cl. .......................................... 702/45; 702/33

(58) Field of Classification Search ............... 73/19.03, 73/54.24, 54.41, 61.45, 61.75, 61.79; 702/33, 702/45, 127, 141, 12, 50, 100
See application file for complete search history.

(56) References Cited

U.S. PATENT DOCUMENTS

| | | |
|---|---|---|
| RE31,450 E | 11/1983 | Smith |
| 4,422,338 A | 12/1983 | Smith |
| 4,491,025 A | 1/1985 | Smith et al. |
| 4,524,610 A * | 6/1985 | Fitzgerald et al. ......... 73/54.25 |
| 4,679,947 A | 7/1987 | Miller et al. |
| 4,817,448 A | 4/1989 | Hargarten et al. |
| 4,852,395 A | 8/1989 | Kolpak |
| 4,876,897 A | 10/1989 | DeCarlo et al. |
| 4,879,911 A | 11/1989 | Zolock |
| 4,911,006 A | 3/1990 | Hargarten et al. |
| 4,934,196 A | 6/1990 | Romano |
| 4,996,871 A | 3/1991 | Romano |
| 5,027,662 A | 7/1991 | Titlow et al. |
| 5,029,482 A | 7/1991 | Liu et al. |
| 5,228,327 A | 7/1993 | Bruck |
| 5,259,250 A | 11/1993 | Kolpak |

(Continued)

FOREIGN PATENT DOCUMENTS

WO   WO 02/08703   1/2002

OTHER PUBLICATIONS

Wenger, A; "Vibrating Fluid Densimeters: A Solution To The Viscosity Problem"; IEEE Transactions on Industrial Electroincs an Control Instrumentation; vol. 1 IECI-27 No. 3; pp. 247-253.*

(Continued)

*Primary Examiner*—John Barlow
*Assistant Examiner*—Douglas N. Washburn
(74) *Attorney, Agent, or Firm*—Fish & Richardson P.C.

(57) ABSTRACT

A digital flowmeter can include a vibratable conduit with a mixture of a liquid and a gas flowing therethrough. A driver can be connected to the conduit and can be operable to impart motion to the conduit where a sensor can also be connected and can be operable to sense the motion of the conduit. A digital transmitter can also be connected to the conduit and can include a void fraction determination system configured to determine a gas void fraction of the mixture, a viscosity determination system configured to determine a viscosity of the liquid in the mixture, and a flow parameter correction system operable to determine a flow parameter associated with the flowing mixture, based on the gas void fraction and the viscosity.

40 Claims, 10 Drawing Sheets

U.S. PATENT DOCUMENTS

| | | | |
|---|---|---|---|
| 5,295,084 A * | 3/1994 | Arunachalam et al. | 702/50 |
| 5,301,557 A | 4/1994 | Cage et al. | |
| 5,347,874 A | 9/1994 | Kalotay et al. | |
| 5,359,881 A | 11/1994 | Kalotay et al. | |
| 5,398,215 A * | 3/1995 | Sinha et al. | 367/31 |
| 5,400,653 A | 3/1995 | Kalotay | |
| 5,469,748 A | 11/1995 | Kalotay | |
| 5,497,666 A | 3/1996 | Patten et al. | |
| 5,535,632 A | 7/1996 | Kolpak | |
| 5,555,190 A | 9/1996 | Derby et al. | |
| 5,594,180 A | 1/1997 | Carpenter et al. | |
| 5,654,502 A | 8/1997 | Dutton | |
| 5,687,100 A | 11/1997 | Buttler et al. | |
| 5,734,112 A | 3/1998 | Bose et al. | |
| 5,821,407 A * | 10/1998 | Sekiguchi et al. | 73/54.28 |
| 5,969,264 A | 10/1999 | Rivkin | |
| 6,006,609 A * | 12/1999 | Drahm et al. | 73/861.357 |
| 6,032,539 A | 3/2000 | Liu et al. | |
| 6,092,429 A | 7/2000 | Cunningham et al. | |
| 6,176,323 B1 * | 1/2001 | Weirich et al. | 175/40 |
| 6,233,526 B1 * | 5/2001 | Cunningham | 702/45 |
| 6,311,136 B1 * | 10/2001 | Henry et al. | 702/45 |
| 6,318,156 B1 | 11/2001 | Dutton et al. | |
| 6,318,186 B1 | 11/2001 | Smith et al. | |
| 6,327,914 B1 | 12/2001 | Dutton | |
| 6,343,507 B1 * | 2/2002 | Felling et al. | 73/152.19 |
| 6,360,579 B1 * | 3/2002 | De Boom et al. | 73/1.35 |
| 6,505,131 B1 | 1/2003 | Henrot | |
| 6,505,519 B1 * | 1/2003 | Henry et al. | 73/861.356 |
| 6,507,791 B1 * | 1/2003 | Henry et al. | 702/45 |
| 6,564,619 B1 | 5/2003 | Dutton et al. | |
| 6,609,067 B1 * | 8/2003 | Tare et al. | 702/9 |
| 6,651,513 B1 * | 11/2003 | Wenger et al. | 73/861.357 |
| 6,754,594 B1 * | 6/2004 | Henry et al. | 702/45 |
| 6,758,102 B1 * | 7/2004 | Henry et al. | 73/861.356 |
| 6,763,730 B1 * | 7/2004 | Wray | 73/861.356 |
| 2002/0033043 A1 | 3/2002 | Dutton et al. | |

OTHER PUBLICATIONS

Reizner, "Coriolis—The Almost Perfect Flow Meter," Colloquium on Coriolis Mass Flow Metering, Oxford, Jun. 2003.

Lamb, H. (1975) "Hydrodynamics" 6$^{th}$ Ed (1975) CUP, p. 505.

Hemp J., Sultan, G. (1989) "On the theory and performance of Coriolis mass flowmeter" Proc of the International Conference on Mass Flow Measurement Direct and Indirect, 1989, Feb. IBC Technical Services, London, 1989.

Lui, R.P., Fuent, M.J., Henry, M.P., Duta, M.D.(2001) "A neural network to correct mass flow errors caused by two phase flow in a digital Coriolis mass flowmeter" Journal of Flow Measurement and Instrumentation, 12 (2001), pp. 53-63.

* cited by examiner

VISCOSITY-CORRECTED FLOWMETER

CROSS-REFERENCE TO RELATED APPLICATIONS

This application claims priority to U.S. Application Ser. No. 60/482,537, filed on Jun. 26, 2003, and titled CORIOLIS FLOWMETER USING INVISCID BUBBLE MODEL FOR TWO PHASE FLOW, which is hereby incorporated by reference.

TECHNICAL FIELD

This description relates to flowmeters.

BACKGROUND

A Coriolis flowmeter is a type of flowmeter, where flowmeters, generally speaking, provide information about materials being transferred through a conduit or flowtube. For example, density meters, or densitometers, provide a measurement of the density of material flowing through a conduit. Additionally, mass flowmeters provide a measurement of the mass of material being transferred through a conduit by, for example, deriving the mass flow measurement from an earlier density measurement and a volumetric flow measurement. Other mass flowmeters may calculate mass flow directly.

Coriolis-type flowmeter systems calculate density and mass flow using the Coriolis effect, in which material flowing through a rotating conduit is affected by a Coriolis force and therefore experiences an acceleration. Many Coriolis mass flowmeter systems induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

In one aspect, a digital flowmeter includes a vibratable conduit with a mixture of a liquid and a gas flowing therethrough. A driver is connected to the conduit and operable to impart motion to the conduit, and a sensor is connected to the conduit and operable to sense the motion of the conduit. A digital transmitter is connected to the conduit and includes a void fraction determination system configured to determine a gas void fraction of the mixture, a viscosity determination system configured to determine a viscosity of the liquid in the mixture, and a flow parameter correction system operable to determine a flow parameter associated with the flowing mixture, based on the gas void fraction and the viscosity.

Implementations may include one or more of the following features. For example, the void fraction determination system may include a void fraction sensor, where the sensor may be contact or non-contact. The viscosity determination system may include an in-line viscometer or an off-line viscometer.

The viscometer may automatically sample the liquid from the mixture and determine a viscosity of the liquid. Alternatively, the liquid may be manually sampled and for determination of the viscosity. The viscosity determination system may be operable to determine a viscosity correction factor for use by the flow parameter correction system in determining the flow parameter.

The flow parameter correction system may include a mathematical model of liquid-gas flow. In this case, the mathematical model may include a bubble model in which the gas is assumed to form bubbles within the liquid, and may include a curve fit model.

The flow parameter correction system may be operable to correct errors in an apparent density or apparent mass flow rate detected by the digital flowmeter. The flow parameter correction system may include a mathematical model of liquid-gas flow for correcting errors in an apparent mass flow rate detected by the digital flowmeter. Such a model may include, for example, a bubble model in which the gas is assumed to form bubbles within the liquid, or a curve fit model.

The digital transmitter may include a self-contained modular unit, and may be operable to communicate with external devices and systems including a central control system.

According to another aspect, a digital transmitter includes a transceiver configured to send signals to, and receive signals from, sensors monitoring a vibrating flowtube and a liquid-gas mixture flowing therein. The digital transmitter also includes an apparent flow parameter determination system that is operable to generate apparent flow parameter values of the mixture from the signals, and a flow parameter correction system operable to correct the apparent flow parameter values, based on a viscosity of the liquid within the liquid-gas mixture.

Implementations may include one or more of the following features. For example, a viscosity determination system may be included that is operable to determine the viscosity, and is further operable to determine a viscosity correction factor based on the viscosity for use by the flow parameter correction system.

The digital transmitter may include a void fraction determination system that is operable to determine a void fraction of the gas within the liquid-gas flow, where the flow parameter correction system may be operable to correct the apparent flow parameter values, based on the void fraction.

The flow parameter correction system may include a mathematical model for correcting an apparent density generated by the apparent flow parameter system. The mathematical model may include a bubble model that assumes bubble flow of the gas within the liquid of the liquid-gas mixture. In addition, the mathematical model may include a curve fit model.

The flow parameter correction system may include include a mathematical model for correcting an apparent mass flowrate generated by the flow parameter system. The mathematical model may include a bubble model that assumes bubble flow of the gas within the liquid of the liquid-gas mixture. In addition, the mathematical model may include a curve fit model.

In another aspect, an apparent flow parameter of a liquid-gas mixture flowing through a vibrating flowtube is determined, and a viscosity of the liquid is determined to thereby determine a viscosity correction factor. An error in the apparent flow parameter may be determined, based upon the viscosity correction factor, and the error in the apparent flow parameter may be corrected.

Implementations may include one or more of the following features. For example, in determining the apparent flow parameter, an apparent density or mass flowrate of the mixture may be determined by observing the deflection of the vibrating flowtube. The viscosity may be determined by exposing an in-line viscometer to the liquid, or by providing a sample of the liquid to a viscometer. The viscosity correction factor may be determined using a bubble model that assumes that the gas within the liquid-gas mixture is contained as bubbled within the mixture. The model may include using a curve fit to correct the error.

The details of one or more implementations are set forth in the accompanying drawings and the description below. Other features will be apparent from the description and drawings, and from the claims.

DETAILED DESCRIPTION

In general, the term flowtube as used herein refers to the flowtube and any associated mechanical parts, drivers, and sensors, while the term "transmitter" refers to the electronics for producing drive signals to control the flowtube oscillations and calculating the properties of the material flowing through the flowtube based on signals received from the sensors. Additionally, the term Coriolis flowmeter may generally refer to a combination of flowtube and transmitter.

U.S. Pat. No. 6,311,136, which is hereby incorporated by reference, discloses the use of a digital flowmeter system and related technology. Such digital flowmeter systems are very precise in their measurements, with little or negligible noise, and are capable of enabling a wide range of positive and negative gains at the driver circuitry for driving the conduit. Such digital flowmeter systems are thus advantageous in a variety of settings. For example, U.S. Pat. No. 6,505,519 discloses the use of a wide gain range, and/or the use of negative gain, to prevent stalling and to more accurately exercise control of the flowtube.

A digital transmitter exchanges sensor and drive signals with its associated conduit or flowtube, so as to both sense an oscillation of the flowtube, and to drive the oscillation of the flowtube accordingly. By quickly and accurately determining the sensor and drive signals, the digital transmitter may provide for fast and accurate operation of the flowtube in determining characteristics of the flow including a mass flow rate of the flow.

Although digital flowmeter systems are discussed above, it should be understood that analog Coriolis flowmeter systems also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a Coriolis flowmeter system uses various control systems and related elements to measure a mass flow, density, and/or other parameters of a material(s) moving through a flowtube or other conduit.

Figure 1A:
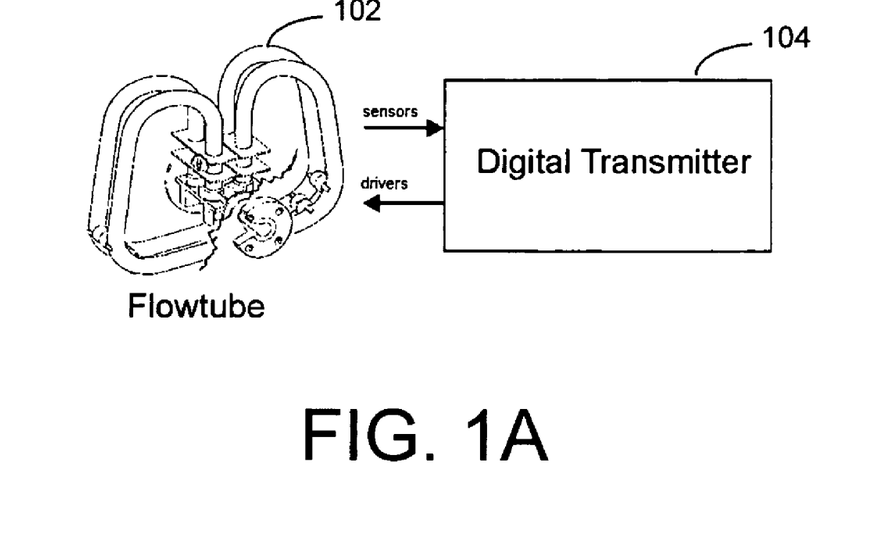
FIG. 1A is an illustration of a Coriolis flowmeter using a bent flowtube.

FIG. 1A is an illustration of a digital flowmeter using a bent flowtube 102. Specifically, the bent flowtube 102 may be used to measure one or more physical characteristics of, for example, a (traveling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the digital transmitter 104 being used with a bent flowtube are provided in, for example, commonly-assigned U.S. Pat. No. 6,311,136.

Figure 1B:
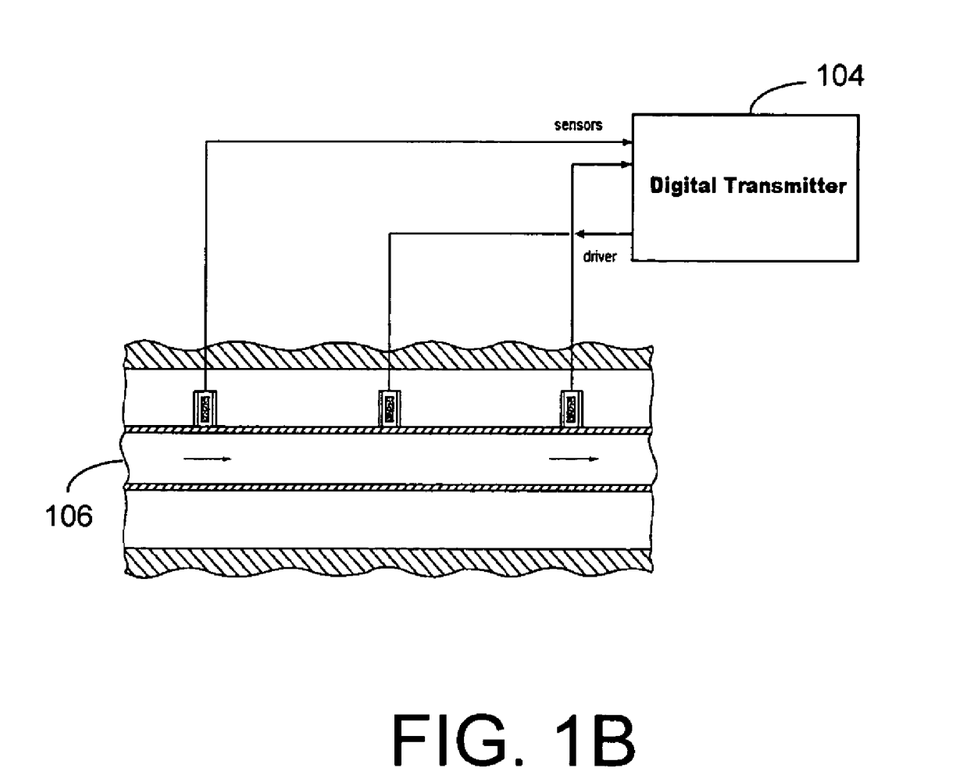
FIG. 1B is an illustration of a Coriolis flowmeter using a straight flowtube.

FIG. 1B is an illustration of a digital flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50–110 Hz, while the straight flowtube 106 may operate at a frequency of, for example, 300–1,000 Hz.

Figure 2:
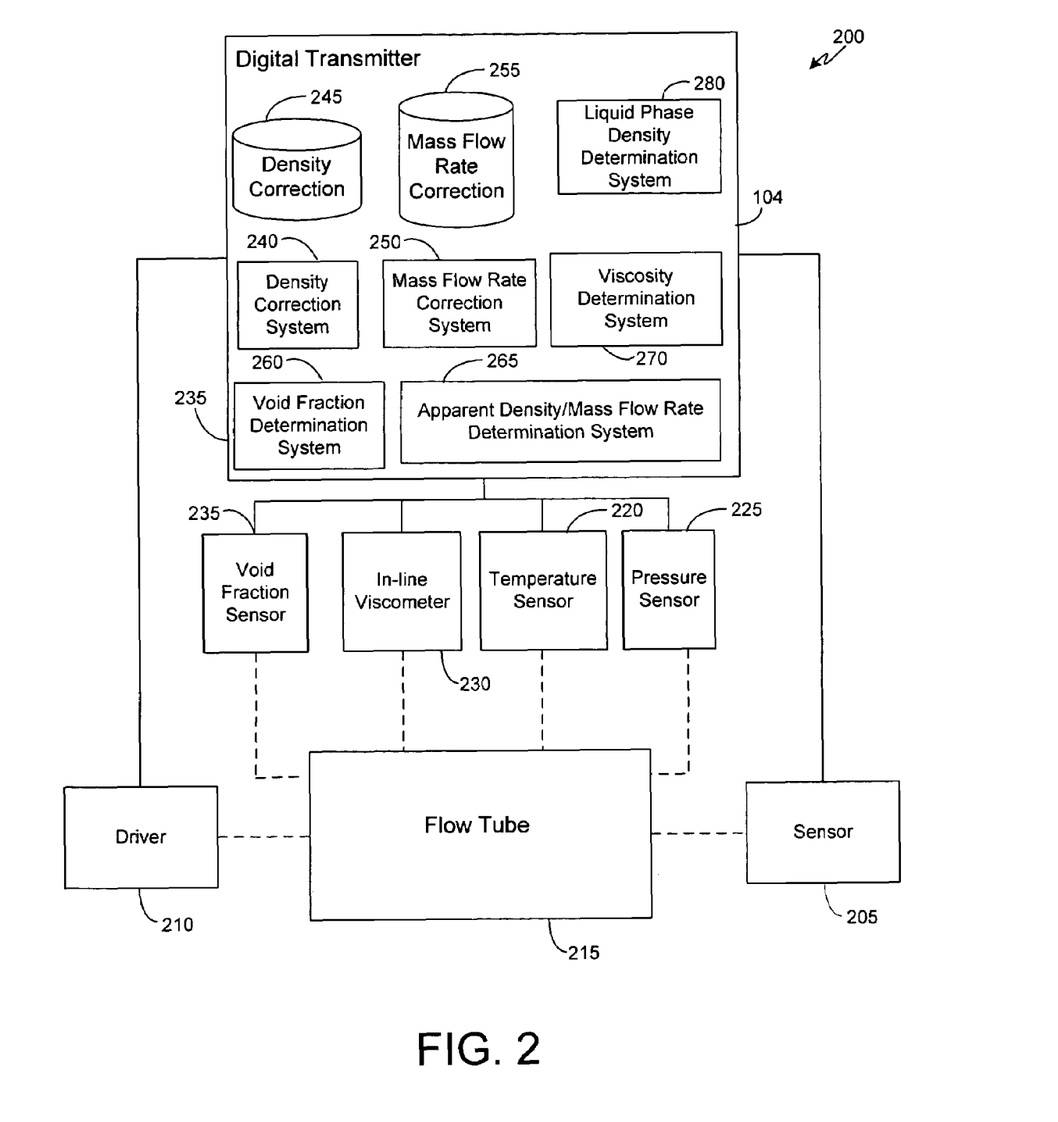
FIG. 2 is a block diagram of a Coriolis flowmeter configured for liquid-gas flow.

Referring to FIG. 2, in one implementation, a digital mass flowmeter 200 includes a digital transmitter 104. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. The digital flowmeter also may include one or more motion sensors 205, one or more drivers 210, and a flowtube 215 (which also may be referred to as a conduit, and which may represent either the bent flowtube 102, the straight flowtube 106, or some other type of flowtube). Additional sensors may be included and may include a temperature sensor 220, a pressure sensor 225, an in-line viscometer 230, and a gas void fraction sensor 235. The gas void fraction sensor 235 may be used when a fluid flow through the flowtube 215 includes both a liquid and a gas, such as, for example, a liquid containing air bubbles. This condition is also referred to as "two-phase flow."

Various techniques exist for measuring the gas void fraction. For example, various sensors or probes exist that may be inserted into the flow to determine a gas void fraction. As another example, a venturi tube (i.e., a tube with a constricted throat that determines fluid pressures and velocities by measurement of differential pressures generated at the throat as a fluid traverses the tube), relying on the fact that gas generally moves with a higher velocity than liquid(s) through a restriction, may be used to determine a pressure gradient and thereby allow a determination of the gas void fraction. In some systems, measurements of gas void fractions may be obtained using equipment (e.g., the gas void fraction sensor 235) that is wholly external to the flowtube. For example, sonar measurements may be taken to determine gas void fraction. As a specific example of such a sonar-based system, the SONARtrac™ gas void fraction monitoring system produced by CiDRA Corporation of Wallingford, Conn. may be used.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

It should be understood that both the pressure of the fluid entering the flowtube 215 and the pressure drop across relevant points on the flowtube may be indicators of certain flow conditions. Also, while external temperature sensors may be used to measure the fluid temperature, such sensors may be used in addition to an internal flowmeter sensor designed to measure a representative temperature for flowtube calibrations. Also, some flowtubes use multiple temperature sensors for the purpose of correcting measurements for an effect of differential temperature between the process fluid and the environment (e.g., a case temperature of a housing of the flowtube).

The digital transmitter 104 can include a variety of measurement and calculation systems. For example, the digital transmitter can include an apparent density and mass flow rate determination system 265. The system 265 can generate raw (i.e., uncorrected) values for the density and mass flow rate of the two-phase flow in flowtube 215 for any of several parameters that may affect the true value of these characteristics. For example, the temperature can affect the value of density for both the liquid phase and the gas phase. Also, two-phase flow itself may result in incorrect apparent readings for density or mass flow.

The apparent density and mass flowrate can be corrected by the density correction system 240 and the mass flow rate correction system 250, as discussed in more detail below. The density correction database 245 and the mass flow rate correction 255 database should be understood to contain, for example, values generated by the correction systems 240 and 250, based upon corrections taking into account any of a number of parameters including, for example, temperature, pressure, void fraction, and viscosity.

FIG. 2 represents one implementation that includes a void fraction determination system 260, a viscosity determination system 270, and a liquid phase density determination system 280. Each of these systems may represent, for example, systems that interpret actual sensor data and generate values of the parameter to feed the correction systems 240 and 250, or, as another example, they may represent systems that generate the parameter data from stored information, or by comparing the stored information to the data gathered or input for other physical parameters. For example, in one embodiment the liquid phase density system 280 can produce a value for the density of water at a specific temperature and pressure based on the measured values of temperature and pressure from sensors 220 and 225, and/or from tabular data for water stored in system 280.

In another implementation, a sample of the process liquid can be brought to the actual operating pressure and temperature, and the density can be measured off-line using a densitometer or other device known to those skilled in the art of density determination, and the determined value can be returned to the transmitter 104 either by the system 280 or by physical input of the data. Thus, the parameter determination systems may include off-line measurement systems or in-line determination systems, and may include systems that connect online devices to the transmitter 104. Such connections can be any of the well-known data transfer connections such as, for example, direct wire connections, wireless connections including optical and RF connections, modem connections, DSL, cable and any other methods of transferring data between two devices.

In one implementation, FIG. 2 includes the in-line viscometer 230 for determining the liquid viscosity in cooperation with the viscosity determination system 270. The liquid viscosity could be determined by the determination system 270 and an off-line viscometer or rheometer, or could be calculated based on other known physical data, or taken from previously tabulated data.

Liquid viscosity may be accounted for when monitoring and measuring two-phase gas-liquid flow as discussed herein. The digital transmitter 104 may then correct the initially calculated output values for density and mass flow rate, using density and mass flowrate correction systems 240 and 250. For example, systems 240 and 250 may have correction models programmed into them. These correction models can be calculable mathematical models, as discussed in more detail below. The correction models also may include historical curve fit models stored in the systems 240 and 250 or can be a combination of a curve fit model and a mathematical model. For example, a correction model may be implemented for conditions where curve fitting data is either not available or where the curve fit is no longer an accurate representation of an existing flow regime, while the curve fit is used where it is accurate and available. Additionally, the models may be used simultaneously, producing multiple corrected values for density and flowrate As referred to above, a Coriolis flowmeter may, by means of resonant frequency, determine the density of a process fluid in the flowtube 215. That is, an accurate bulk density of the process fluid can typically be determined. In some situations, the process fluid is a binary mixture of two materials, such as, for example, oil and water. In such cases, also referred to as "two-phase flows," a relative percentage of each constituent may be determined using, for example, an algebraic sum or an algorithm relating density to composition.

Another example of two-phase flow includes a liquid-gas flow, in which the gas forms bubbles flowing within the liquid and through the flowtube. In this case, the density and mass flow solutions become more complex, and error may be introduced in calculating the mass flow and density as a result of operating difficulties and measurement errors. Accordingly, as referred to above, a model may be constructed that assumes such bubble flow and that accounts for, for example, a gas void fraction resulting from the bubble flow and/or a viscosity of the liquid within the two-phase flow.

Figure 3:
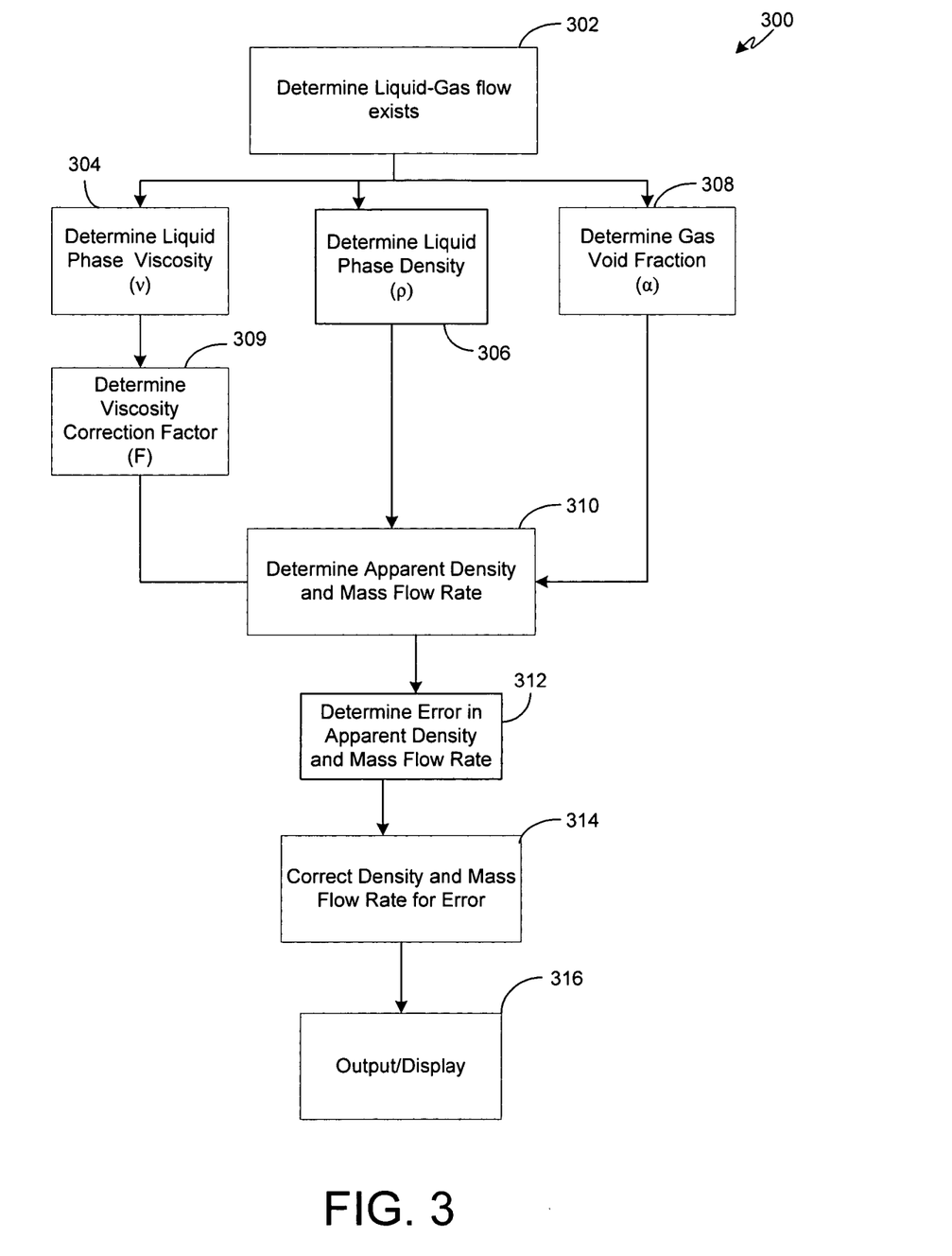
FIG. 3 is a flowchart illustrating a process for correcting density and/or mass flow measurement in a two-phase flow.

FIG. 3 is a flowchart illustrating a process for correcting density and/or mass flow measurement in a two-phase flow. In FIG. 3, first it is determined that two-phase, liquid-gas flow exists within the flow meter (302), which can be determined, for example, through observation, or by monitoring the gas void fraction sensor 235 and observing the values for gas void fraction generated.

The liquid phase viscosity is determined (304), as well as the liquid phase density (306) and the gas void fraction (308), using, for example, the corresponding sensors and systems discussed above with respect to FIG. 2. Some of these parameters may be dependent on other additional parameters such as temperature or pressure, which can also be measured or calculated using, for example, the systems and sensors of FIG. 2. The viscosity may then be used to determine a viscosity correction factor (309), referred to as the factor "F" below.

When an apparent density or mass flow rate is determined (310), then, the correction factor F and some or all of the other determined parameters may be used to determine an error in the apparent values (312). As a result, a corrected density and mass flow rate may be determined (314).

The following discussion provides examples of techniques for implementing the systems and techniques of FIGS. 2 and 3. In particular, a mathematical model is described and derived that may be used with the systems and techniques of FIGS. 2 and 3 to correct flowmeter measurements for density and mass flow during a two-phase, liquid-gas flow in the flowmeter.

Figure 4:
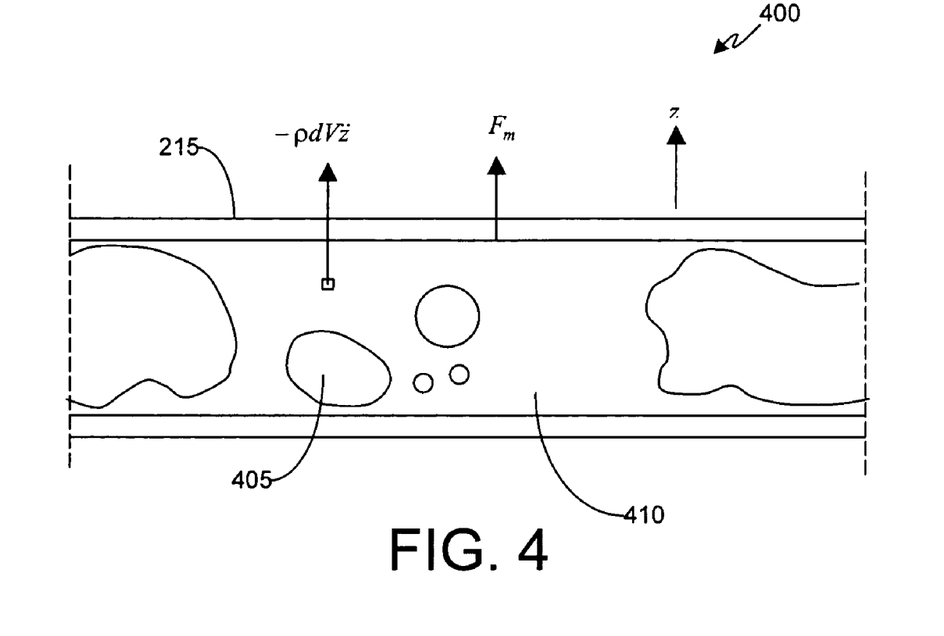
FIG. 4 is an example of two-phase flow in a flowtube.

FIG. 4 indicates a short section of Coriolis mass flowmeter tube 400 through which two-phase flow is taking place indicated by bubbles 405 and liquid 410. The tube is undergoing a small amplitude sinusoidal vibration in the z direction (the displacement being the distance z from the static equilibrium position of the tube). It is assumed that the vibrational frequency is so high that during one cycle of vibration the interfaces between the phases do not change geometrically and move along the tube over a small distance compared to the length of the tube section. The inertia reaction forces can thus be calculated as if the gas/liquid mixture was suspended in its motion along the tube (i.e. disregarding gravitational forces and surface tension, and flow). Taking coordinates moving with the tube, each liquid element dV experiences an inertia force $-\rho dVz(-\rho dV\ddot{z})$ in the z-direction giving rise to a small vibrational flow of the liquid and a corresponding reaction force $F_m$ on the tube:

$F_m = -\rho z A_m (\rho \ddot{z} A_m)$ or in the complex notation $F_m = \rho \omega^2 z A_m$ per unit length of the tube m, which reduces to $A_m = A$ the tubes internal cross-sectional area, for single-phase flow.

Considering the same section of flowtube and taking the coordinates moving up and down and turning with the tube, the reaction force to the Coriolis force field in the liquid can be derived to be:

$F_c = -i2\rho \omega v \delta z/\delta s A_c$ where v is the mean flow velocity related to the total volumetric flow rate $Q_L$ by:

$Q_L = (1-\alpha) v A$

Because in Coriolis flow meters velocity distribution effects are known to be very small, $A_c$ dependence on liquid velocity distribution is negligible. Thus, $A_c$ is the same as if v was everywhere constant and equal to the mean v. This results in the inertia and Coriolis forces being uniform throughout the liquid so that the effective areas are equal.

$A_m = A_c$ to a good approximation.

Considering a small mass-less bubble in a liquid filled container undergoing simple harmonic motion in the z-direction, a linear fluid mechanics treatment of the problem results in the reaction force of the bubble on the container results in:

$F_z = -4/3 \pi a^3 \rho \omega^2 z F$ where a is the bubble radius, $\rho$ is the liquid density, $\omega$ is the angular frequency of the harmonic motion $(=2\pi f)$, z is the displacement amplitude in the +ve z-direction and F, i.e., the viscosity correction factor discussed above with respect to FIG. 3, is a factor depending only on the non-dimensional complex constant $\zeta$ given by:

$\zeta = -a/\delta(-1+i)$ where $\delta = (2v/\omega)^{0.5}$ v being the kinematic viscosity of the liquid. The expression of F in terms of $\zeta$ is $$F = 1 + \zeta^2 \frac{-\frac{1}{3}\zeta(2f_0'(\zeta) - \zeta^2 f_2'(\zeta) + \zeta f_2(\zeta)) + 2(f_0(\zeta) + \zeta^2 f_2(\zeta))}{\frac{1}{6}(-\zeta^2 + 12\zeta)(2f_0'(\zeta) - \zeta^2 f_2'(\zeta) + \zeta f_2(\zeta)) + 4\zeta(f_0'(\zeta) + \zeta^2 f_2'(\zeta) + 2\zeta f_2(\zeta))} \quad (1)$$

where $$f_0(\zeta) = \frac{e^{-i\zeta}}{\zeta}, \quad f_2(\zeta) = \left(-\frac{1}{\zeta^3} + \frac{3i}{\zeta^4} + \frac{3}{\zeta^5}\right) e^{-i\zeta} \quad (2)$$

and a prime denotes 'the derivative of'.

Figure 5:
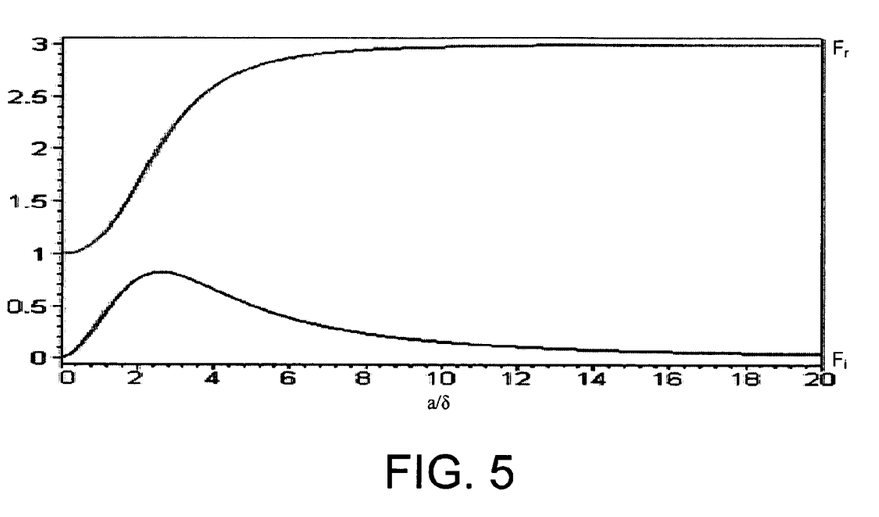
FIG. 5 is a graph of a viscosity correction factor.

The real and imaginary parts $F_r$ and $F_i$ of F are plotted in FIG. 5 as a function of $a/\delta$. In the zero viscosity limit $v \to 0$, $F=3$ so that $F_z$ becomes three times the volume of the bubble times $-\rho \omega^2 z$ ($\equiv \rho \ddot{z}$). In the extreme limit of very high viscosity $v \to \infty$, $F=1$.

Modeling bubble flow in a Coriolis flowmeter tube as a number of small non-interacting bubbles moving with the liquid at one speed (no bubble slip velocity), the inertia reaction force $F_m$ on the tube section due to the liquid and a single bubble inside it is $$F_m = \rho V \omega^2 z - \frac{4}{3} \pi a^3 \rho \omega^2 z F,$$

where V is the volume of the tube section interior. The inertia reaction force due to several bubbles in the tube section is $$F_m = \rho V \omega^2 z \left(1 - \sum \frac{\frac{4}{3}\pi a^3}{V} F\right)$$

where the sum extends over all the bubbles in the tube section. In the summation, a and F depend on bubble size. In terms of void fractions $\alpha_n$ for bubbles of radius $a_n$, n=1,2,3 ... N results in $$F_m = \rho A \omega^2 z \left(1 - \sum_{n=1}^{N} \alpha_n F_n\right)$$

per unit length of tube where A is the internal area of cross-section of the tube. Then an effective area for inertia may be written as $$A_m = \left(1 - \sum_{n=1}^{N} \alpha_n F_n\right) A$$

also giving the effective area $A_c$.

Two extreme conditions are described below for the sake of illustration.

1. When viscosity tends to zero, $F_n \to 3$ and the effective area becomes $(1-3\alpha)A$ with $$\alpha = \sum_{n=1}^{N} \alpha_n.$$

$F_m = \rho \omega^2 z A_m = \rho \omega^2 z (1-3\alpha) A$ per unit length of tube $$F_c = -i2\omega \rho v \frac{\partial z}{\partial s} A_c = -i2\omega \rho v \frac{\partial z}{\partial s}(1-3\alpha)A$$

per unit length of tube

Therefore (before any correction) the meter measures apparent density $\rho_a$ and apparent mass flow rate $\dot{m}_a$ given by $\rho_a = \rho(1-3\alpha)$ $\dot{m}_a = \rho v A(1-3\alpha)$      (3).

If it is assumed that the density p of the liquid is known and that an apparent density measurement is made by the meter then the density error is given by $$E_d = -\frac{\rho_a - \rho}{\rho} = 3\alpha$$

Since the true mass flow rate is given by $\dot{m} = \rho(1-\alpha)vA$ the mass flow fractional error (neglecting the mass of the gas) $E_{\dot{m}}$ is $$E_{\dot{m}} = \frac{\dot{m}_a - \dot{m}}{\dot{m}} = -\frac{2\alpha}{1-\alpha}.$$

2. In the extreme case of very tiny bubbles or very viscous liquid $F_n \to 1$ for all n and $A_m = A_c = (1-\alpha)A$ The reaction forces are $F_m = \rho \omega^2 z(1-\alpha)A$ $$F_c = -i2\omega \rho v \frac{\partial z}{\partial s}(1-\alpha)A$$

The apparent density and apparent mass flow rate are given by $\rho_a = (1-\alpha)\rho$ $\dot{m}_a = \rho v A(1-\alpha)$ giving:

$E_d = \alpha$ $E_{\dot{m}} = 0$.

This suggests that, with the gas density negligible compared with that of the liquid, the density and mass flow registered by the Coriolis meter is the density and mass flow of gas and liquid mixture being homogeneous and with no slip between the phases.

Figure 6:
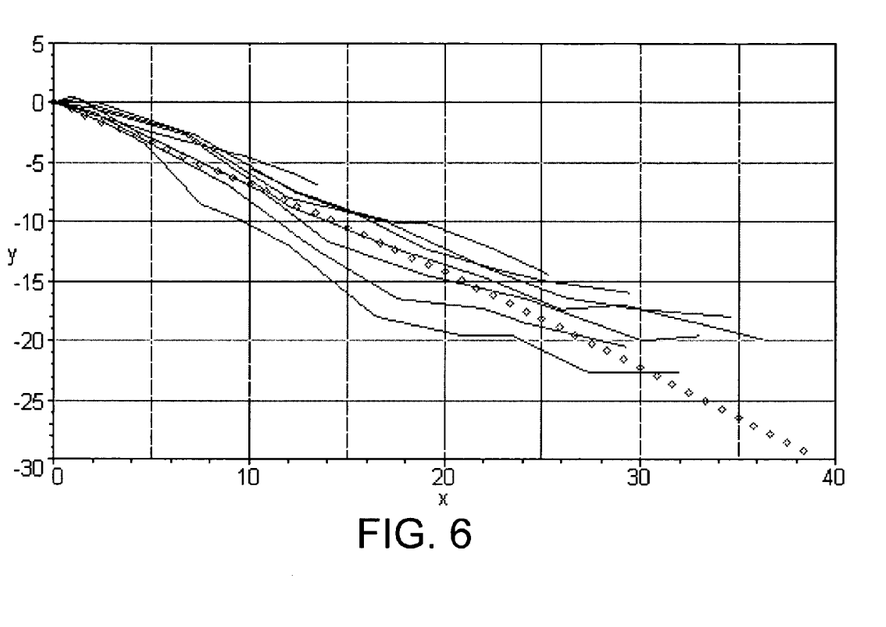
FIG. 6 is a graph comparing predicted values using a bubble model with experimental results.

FIG. 6 is a graph comparing predicted values using the bubble model just described with experimental results. As can be seen from the graph the bubble model correlates reasonably with the experimental results, and results in a significant drop in the mass flow measurement error. For example, at a flow rate of 1.5 kg/s and a void fraction of 3.3% the measurement error is reduced from about 10% without the viscosity correction to about 3% with the correction. Similarly, for a void fraction of about 6.7%, the mass flow rate measurement error is reduced from about 19% to about 5%.

Figure 7:
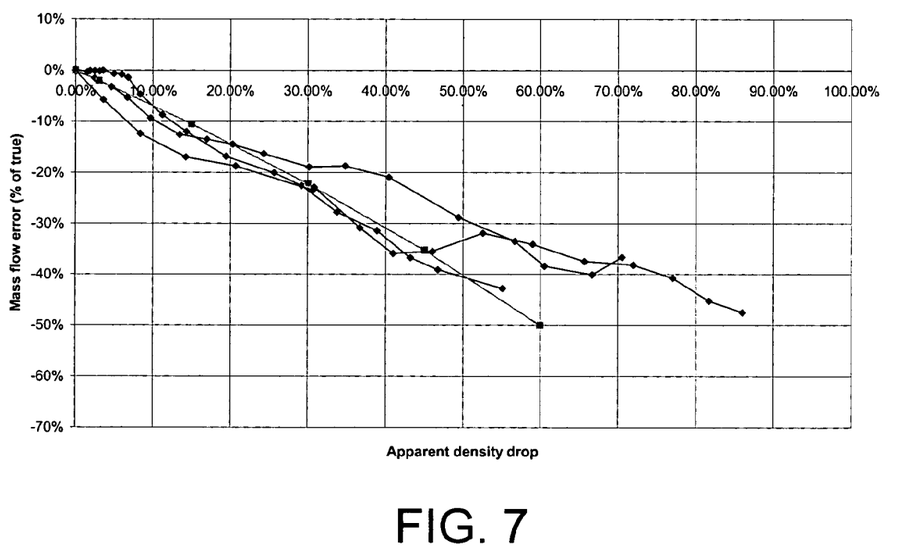
FIG. 7 is a graph comparing mass flow error with the drop in density for a series of set liquid flows versus the predicted error.

FIG. 7 is a graph comparing mass flow error with the drop in density for a series of set liquid flows versus the predicted error from the viscosity corrected model. As can be seen, the mass flow error is small for small gas void fractions of up to about 5%.

Figure 8:
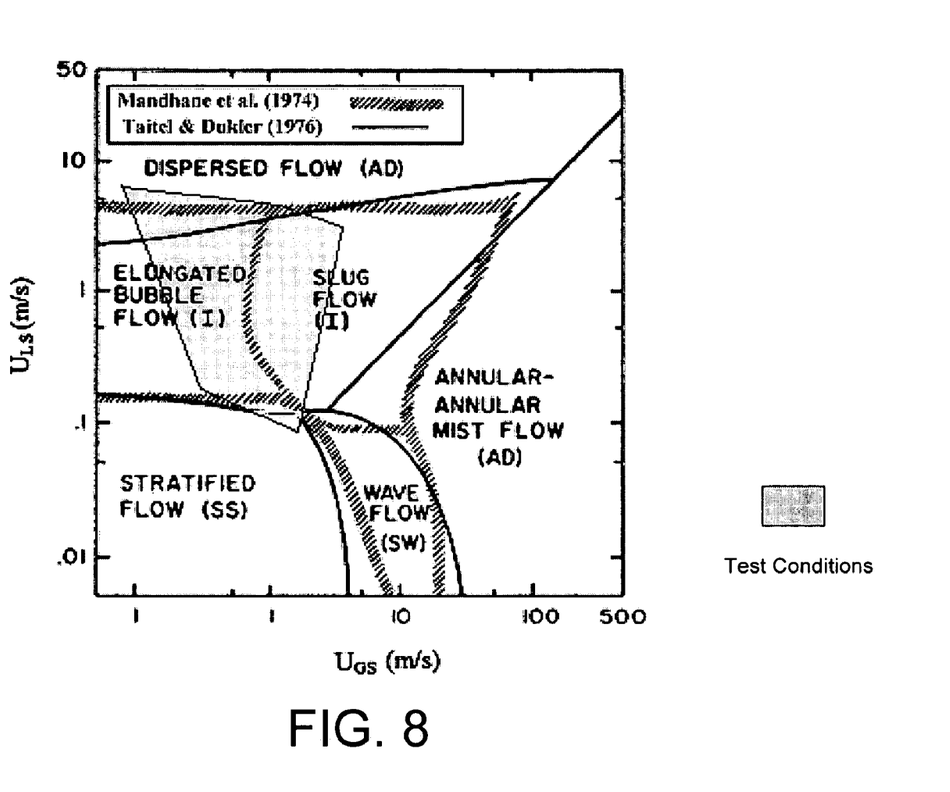
FIG. 8 is a map representing gas-liquid flow regimes representing the flow conditions used in testing the model.

FIG. 8 is a map representing gas-liquid flow regimes used in testing the model. In FIG. 8, test conditions are shown under which experiments described herein were generally conducted. However, it should be understood that the results described herein may be generally applicable to other conditions and/or flow regimes.

Figure 9:
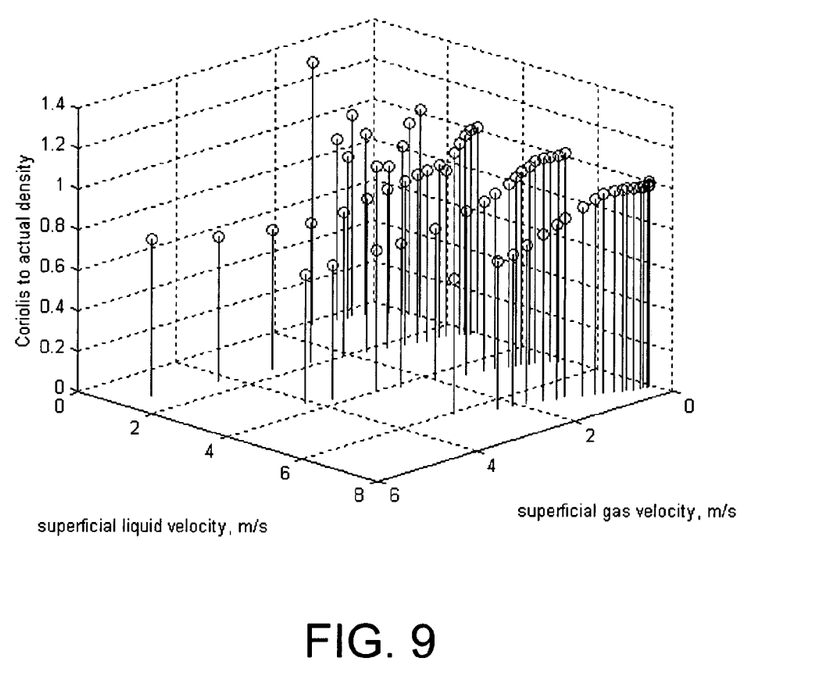
FIG. 9 is a graph comparing a ratio of an actual density to a measured density.
Figure 10:
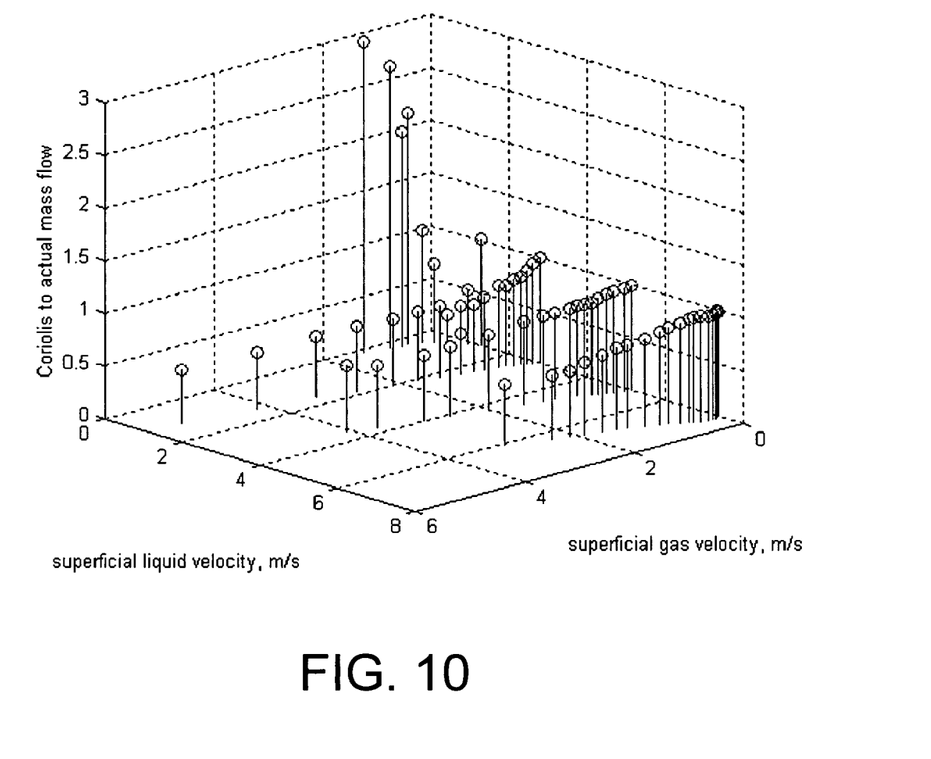
FIG. 10 is a graph comparing a ratio of an actual mass flow rate to a measured mass flowrate.

FIG. 9 is a graph comparing a ratio of an actual density to a measured density, and FIG. 10 is a graph comparing a ratio of an actual mass flow rate to a measured mass flowrate. In FIGS. 9 and 10, superficial liquid and gas velocities are illustrated.

A number of implementations have been described. Nevertheless, it will be understood that various modifications may be made. For example, additional methods of measurement, and types of sensors could be used, and other correction models may be used. Accordingly, other implementations are within the scope of the following claims.

What is claimed is:
1. A digital flowmeter comprising:
   a vibratable conduit with a mixture of a liquid and a gas flowing therethrough;
   a driver connected to the conduit and operable to impart motion to the conduit;
   a sensor connected to the conduit and operable to sense the motion of the conduit; and a digital transmitter connected to the conduit and comprising,
  a void fraction determination system configured to determine a gas void fraction of the mixture;
  a viscosity determination system configured to determine a viscosity of the liquid in the mixture; and
  a flow parameter correction system operable to determine a flow parameter associated with the flowing mixture, based on the gas void fraction and the viscosity.

2. The digital flowmeter of claim 1 wherein the void fraction determination system comprises a void fraction sensor.

3. The digital flowmeter of claim 1 wherein the viscosity determination system comprises an in-line viscometer.

4. The digital flowmeter of claim 1 wherein the viscosity determination system comprises an off-line viscometer.

5. The flowmeter of claim 4 wherein the viscometer automatically samples the liquid from the mixture and determines a viscosity of the liquid.

6. The flowmeter of claim 4 wherein the liquid is manually sampled and the viscosity is determined.

7. The flowmeter of claim 1 wherein the viscosity determination system is operable to determine a viscosity correction factor for use by the flow parameter correction system in determining the flow parameter.

8. The digital flowmeter of claim 1 wherein the flow parameter correction system comprises a mathematical model of liquid-gas flow.

9. The digital flowmeter of claim 8 wherein the mathematical model comprises a bubble model in which the gas is assumed to form bubbles within the liquid.

10. The digital flowmeter of claim 9 wherein the mathematical model further comprises a curve fit model.

11. The digital flowmeter of claim 1 wherein the flow parameter correction system is operable to correct errors in an apparent density detected by the digital flowmeter.

12. The digital flowmeter of claim 1 wherein the flow parameter correction system comprises a mathematical model of liquid-gas flow for correcting errors in an apparent mass flow rate detected by the digital flowmeter.

13. The digital flowmeter of claim 12 wherein the mathematical model comprises a bubble model in which the gas is assumed to form bubbles within the liquid.

14. The digital flowmeter of claim 13 wherein the mathematical model further comprises a curve fit model.

15. The digital flowmeter of claim 1 wherein the flow parameter correction system corrects errors in an apparent mass flowrate detected by the digital flowmeter.

16. The digital flowmeter of claim 1 wherein the digital transmitter comprises a self-contained modular unit.

17. The digital flowmeter of claim 1 wherein the digital transmitter is operable to communicate with external devices and systems.

18. The digital flowmeter of claim 17 wherein the digital transmitter is operable to communicate with a central control system.

19. A digital transmitter comprising:
  a transceiver configured to send signals to, and receive signals from, sensors monitoring a vibrating flowtube and a liquid-gas mixture flowing therein;
  an apparent flow parameter determination system to generate apparent flow parameter values of the mixture from the signals, wherein the apparent flow parameter values reflect an apparent density or an apparent mass flow rate of the mixture; and
  a flow parameter correction system operable to correct the apparent flow parameter values, based on a viscosity of the liquid within the liquid-gas mixture.

20. The transmitter of claim 19 further comprising a viscosity determination system that is operable to determine the viscosity, and further operable to determine a viscosity correction factor based on the viscosity for use by the flow parameter correction system.

21. The transmitter of claim 19 further comprising a void fraction determination system that is operable to determine a void fraction of the gas within the liquid-gas flow, wherein the flow parameter correction system is operable to correct the apparent flow parameter values, based on the void fraction.

22. The transmitter of claim 19 wherein the flow parameter correction system comprises a mathematical model for correcting an apparent density generated by the apparent flow parameter system.

23. The transmitter of claim 22 wherein the mathematical model comprises a bubble model that assumes bubble flow of the gas within the liquid of the liquid-gas mixture.

24. The transmitter of claim 23 wherein the mathematical model further comprises a curve fit model.

25. The transmitter of claim 19 wherein the flow parameter correction system comprises a mathematical model for correcting an apparent mass flowrate generated by the flow parameter system.

26. The transmitter of claim 25 wherein the mathematical model comprises a bubble model that assumes bubble flow of the gas within the liquid of the liquid-gas mixture.

27. The transmitter of claim 26 wherein the mathematical model further comprises a curve fit model.

28. A method comprising:
  determining an apparent flow parameter of a gas-liquid mixture flowing through a vibrating flowtube;
  determining a viscosity of the liquid;
  determining a viscosity correction factor;
  determining an error in the apparent flow parameter, based upon the viscosity correction factor; and
  correcting the error in the apparent flow parameter.

29. The method of claim 28 wherein determining the apparent flow parameter comprises determining an apparent density or mass flowrate of the mixture by observing a deflection of the vibrating flowtube.

30. The method of claim 28 wherein determining the viscosity of the liquid comprises exposing an in-line viscometer to the liquid.

31. The method of claim 28 wherein determining the viscosity of the liquid comprises providing a sample of the liquid to a viscometer.

32. The method of claim 28 wherein determining a viscosity correction factor comprises calculating a correction factor using a bubble model that assumes that the gas within the liquid-gas mixture is contained as bubbles within the mixture.

33. The method of claim 28 wherein correcting the error in the apparent flow parameter comprises using a curve fit to correct the error.

34. A digital transmitter comprising:
  at least one processing device, the processing device configured to perform the following operations:
  determine an apparent flow parameter of a gas-liquid mixture flowing through a vibrating flowtube;
  determine a viscosity of the liquid;

determine a viscosity correction factor;
determine an error in the apparent flow parameter, based upon the viscosity correction factor; and
correct the error in the apparent flow parameter.

35. The method of claim 34 wherein, to determine the apparent flow parameter, the processing device is configured to determine an apparent density or mass flowrate of the mixture by observing a deflection of the vibrating flowtube.

36. The method of claim 34 wherein, to determine the viscosity of the liquid, the processing device is configured to receive a reading from an in-line viscometer exposed to the liquid.

37. The method of claim 34 wherein, to determine a viscosity correction factor, the processing device is configured to calculate a correction factor using a bubble model that assumes that the gas within the liquid-gas mixture is contained as bubbles within the mixture.

38. The method of claim 34 wherein, to correct the error in the apparent flow parameter, the processing device is configured to use a curve fit to correct the error.

39. The method of claim 19 wherein the apparent flow parameter values reflect an apparent density of the mixture and not an apparent mass flow rate of the mixture.

40. The method of claim 19 wherein the apparent flow parameter values reflect an apparent mass flow rate of the mixture and not an apparent density of the mixture.

* * * * *